(12) United States Patent
Sakai et al.

(10) Patent No.: US 6,673,807 B1
(45) Date of Patent: Jan. 6, 2004

(54) IMMUNOSUPPRESSIVE IMIDAZOLE DERIVATIVES AND THEIR COMBINATION PREPARATIONS WITH TACROLIMUS OR CYCLOSPORINS

(75) Inventors: Fumihiko Sakai, Tsukuba (JP); Harumi Yamazaki, Niihari-gun (JP); Noboru Chida, Nishinomiya (JP); Osamu Nakayama, Kitasouma-gun (JP); Yoshihiro Yokota, Nishinomiya (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/646,886

(22) PCT Filed: Apr. 5, 1999

(86) PCT No.: PCT/JP99/01806

§ 371 (c)(1), (2), (4) Date: Dec. 1, 2000

(87) PCT Pub. No.: WO99/51215

PCT Pub. Date: Oct. 14, 1999

(30) Foreign Application Priority Data

Apr. 6, 1998 (AU) .............................................. PP2827
May 4, 1998 (AU) .............................................. PP3324
Aug. 4, 1998 (AU) .............................................. PP5056

(51) Int. Cl.$^7$ .............................................. A61K 31/44
(52) U.S. Cl. ....................... 514/290; 514/291; 514/183; 514/396; 548/100
(58) Field of Search ................................ 514/290, 291, 514/183, 396; 548/100

(56) References Cited

PUBLICATIONS

Plosker, Drugs 59, 323–389, 2000.*
Spencer, Drugs 54, 925–975, 1997.*

* cited by examiner

Primary Examiner—Christopher S. F. Low
Assistant Examiner—David Lukton
(74) Attorney, Agent, or Firm—Leydig, Voit & Mayer, Ltd.

(57) ABSTRACT

Methods for increasing graft survival time comprising administering the combination of a compound that inhibits the production of nitric oxide and a compound that is a tricyclic macrolide, such as tacrolimus.

12 Claims, No Drawings

IMMUNOSUPPRESSIVE IMIDAZOLE DERIVATIVES AND THEIR COMBINATION PREPARATIONS WITH TACROLIMUS OR CYCLOSPORINS

TECHNICAL FIELD

This invention relates to a new use of a compound possessing an inhibitory activity on the production of nitric oxide, which is useful in a medical field.

BACKGROUND ART

Various compounds possessing an inhibitory activity on the production of nitric oxide have already been known, for example, in EP 0 394 989-A2, WO96/16981, WO97/45425, WO98/27108, etc.

DISCLOSURE OF INVENTION

This invention relates to a new use of a compound possessing an inhibitory activity on the production of nitric oxide, for increasing an effect caused by interleukin 2 inhibitor (hereinafter, referred to IL-2 inhibitor).

Therefore, one object of the present invention is to provide a new use of a compound possessing an inhibitory activity on the production of nitric oxide, for increasing an effect caused by IL-2 inhibitor.

Another object of this invention is to provide a method for increasing an effect caused by IL-2 inhibitor by administering an effective amount of a compound possessing an inhibitory activity on the production of nitric oxide.

A further object of this invention is to provide a use of a compound possessing an inhibitory activity on the production of nitric oxide for manufacturing a medicament for increasing an effect caused by IL-2 inhibitor.

Still further object of this invention is to provide a composition comprising a compound possessing an inhibitory activity on the production of nitric oxide, for increasing an effect caused by IL-2 inhibitor.

In the present invention, the "compound possessing an inhibitory activity on the production of nitric oxide" should not be limited and be considered to mean any compounds which have an inhibitory activity on the production of nitric oxide. Preferable one is a compound possessing an inhibitory activity on the production of inducible nitric oxide synthase (iNOS), and the other preferable one is a compound possessing an iNOS-inhibitory activity.

The compound having the following formula (I) are exemplified as a preferable example of the above "compound possessing an inhibitory activity on the production of nitric oxide".

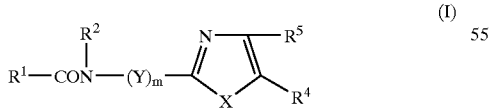

(I)

wherein $R^1$ is indolyl which may have a suitable substituent selected from the group consisting of lower alkyl, phenyl, halogen, lower alkoxy, and nitro, benzofuranyl, phenyl which may have one or two suitable substituent(s) selected from the group consisting of amino, acylamino, lower alkylamino, halogen, lower alkoxy and nitro, lower alkyl, quinoxalinyl, quinolyl, pyrrolyl, pyrimidinyl having benzofuranyl, benzimidazolyl, benzothienyl, benzothiazolyl, benzoxazolyl, indolinyl, anilino, phenylcarbamoyl or imidazolyl which may have one or two suitable substituent(s) selected from the group consisting of phenyl, lower alkyl and indolyl;

$R^2$ is hydrogen or phenyl(lower)alkyl;

$R^4$ is hydrogen, phenyl or pyridyl, each of which may have suitable substituent(s) selected from the group consisting of lower alkyl, lower alkoxy, lower alkylthio, halogen, trihalomethyl, nitro, cyano, imidazolyl, optionally protected hydroxy, acyl, amino, acylamino, diacylamino, di(lower)alkyl-amino, amino (lower)alkyl, acylamino(lower)alkyl, pyrazolyl, morpholinyl, piperidyl, triazolyl, lower alkoxy(lower) alkyl, hydroxy(lower)alkyl, lower alkylpiperazinyl, phenyl and carboxy, quinolyl or 3,4-methylenedioxyphenyl;

$R^5$ is hydrogen, imidazolyl, phenyl, nitrophenyl, phenyl (lower)- alkyl, optionally esterified carboxy or a group of the formula:

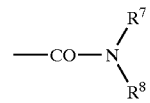

in which $R^7$ and $R^8$ are the same or different and each is hydrogen, phenyl, phenyl(lower)alkyl, lower alkyl or lower alkoxy; or $R^4$ and $R^5$ in combination form a group of the formula:

Y is a group of the formula:

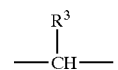

in which $R^3$ is hydrogen or a group of the formula:

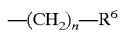

in which $R^6$ is optionally protected hydroxy, acyl, carboxy, acylamino, lower alkoxy, phenyl(lower) alkoxy, lower alkylthio, phenyl which may have a suitable substituent selected from the group consisting of lower alkoxy, halogen, amino, acylamino, diacylamino and nitro, pyridyl which may have a suitable substituent selected from the group consisting of lower alkoxy and halogen, pyrazinyl, pyrimidinyl, furyl, imidazolyl, naphthyl, N-(lower)alkylindolyl or 3,4-methylenedioxyphenyl, and n is an integer of 0 to 3, or a group of the formula:

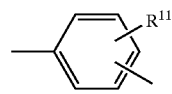

in which $R^{11}$ is phenyl, phenoxy or phenyl(lower) alkoxy; or $R^2$ and $R^3$ in combination form a group of the formula:

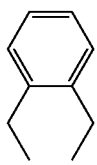

m is 0 or 1; and
X is S or $NR^9$
in which $R^9$ is hydrogen, lower alkyl, cyclo(lower)alkyl or a group of the formula:

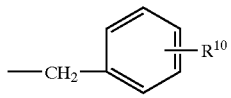

in which $R^{10}$ is hydrogen, lower alkyl or lower alkoxy; or a pharmaceutically acceptable salt thereof.

Suitable pharmaceutically acceptable salts of the compound (I) are conventional non-toxic salts and include, for example, a salt with a base or an acid addition salt such as a salt with an inorganic base, for example, an alkali metal salt (e.g., sodium salt, potassium salt, etc.), an alkaline earth metal salt (e.g., calcium salt, magnesium salt, etc.), an ammonium salt; a salt with an organic base, for example, an organic amine salt (e.g., triethylamine salt, pyridine salt, picoline salt, ethanolamine salt, triethanolamine salt, dicyclohexylamine salt, N,N'-dibenzylethylenediamine salt, etc.); an inorganic acid addition salt (e.g., hydrochloride, hydrobromide, sulfate, phosphate, etc.); an organic carboxylic or sulfonic acid addition salt (e.g., formate, acetate, trifluoroacetate, maleate, tartrate, citrate, fumarate, methanesulfonate, benzenesulfonate, toluenesulfonate, etc.); and a salt with a basic or acidic amino acid (e.g., arginine, aspartic acid, gultamic acid, etc.).

In the above and subsequent descriptions of the present specification, suitable examples and illustration of the various definitions which the present invention intends to include within the scope thereof are explained in detail as follows.

The term "lower" is used to intend a group having 1 to 6, preferably 1 to 4, carbon atom(s), unless otherwise provided.

Suitable "lower alkyl" and "lower alkyl moiety" in the terms "lower alkylthio", "lower alkylthio(lower)alkyl", "N-(lower)alkylindolyl", "lower alkylamino", "di(lower)alkylamino", "phenyl(lower)alkyl", "amino(lower)alkyl", "acylamino(lower)alkyl", "hydroxy(lower)alkyl" and "lower alkylpiperazinyl" include straight or branched one-having 1 to 6 carbon atom(s), such as methyl, ethyl, propyl, isopropyl, butyl, isobutyl, sec-butyl, tert-butyl, pentyl, tert-pentyl andhexyl, in which more preferred one is C1–C4 alkyl.

Suitable "lower alkoxy" and "lower alkoxy moiety" in the terms "lower alkoxy(lower)alkoxy" and "phenyl(lower)alkoxy" include, for example, methoxy, ethoxy, propoxy, isopropoxy, butoxy, isobutoxy, tert-butoxy, pentyloxy, tert-pentyloxy and hexyloxy, in which more preferred one is C1–C4 alkoxy.

Suitable "halogen" includes, for example, fluorine, bromine, chlorine and iodine.

"Optionally esterified carboxy" includes carboxy and esterified carboxy. Suitable examples of said ester include lower alkyl ester(e.g., methyl ester, ethyl ester, propyl ester, isopropyl ester, butyl ester, isobutyl ester, tert-butyl ester, pentyl ester, tert-pentyl ester, hexyl ester, etc.); lower alkenyl ester (e.g., vinyl ester, allylester, etc.); lower alkynyl ester (e.g., ethynyl ester, propynyl ester, etc.); lower alkoxy (lower)alkyl ester (e.g., methoxymethyl ester, ethoxymethyl ester, isopropoxymethyl ester, 1-methoxyethyl ester, 1-ethoxyethyl ester, etc.); mono(or di or tri)aryl(lower)alkyl ester, for example, mono(or di or tri)phenyl(lower)alkyl ester which may have one or more suitable substituent(s) [e.g.,benzyl ester, 4-methoxybenzyl ester, 4-nitrobenzyl ester, phenethyl ester, trityl ester, benzhydryl ester, bis (methoxyphenyl)methyl ester, 3,4-dimethoxybenzyl ester, 4-hydroxy-3,5-di-tert-butylbenzyl ester, etc.]; and aryl ester which may have one or more suitable substituent(s)such as substituted or unsubstituted phenyl ester (e.g., phenyl ester, tolyl ester, tert-butylphenyl ester, xylyl ester, mesityl ester, cumenyl ester, 4-chlorophenyl ester, 4-methoxyphenyl ester, etc.).

Suitable "trihalomethyl" includes, for example, trifluoromethyl,trichloromethyl and tribromomethyl, in which preferred one is trifluoromethyl.

Suitable "amino protective group" includes, for example, acyl and conventional protective group such as mono(or di or tri)aryl(lower)-alkyl, for example, mono(or di or tri) phenyl(lower)alkyl (e.g., benzyl, trityl, etc.).

Suitable "acyl" and "acyl moiety" in the terms "acylamino", "diacylamino" and "acylamino(lower)alkyl" include, for example, carbamoyl which may be substituted by suitable substituent(s), aliphatic acyl group and acyl group containing an aromatic ring, which is referred to as aromatic acyl, or a heterocyclic ring, which is referred to as heterocyclic acyl.

Suitable examples of said acyl are illustrated as follows: "carbamoyl which may be substituted by suitable substituent(s)" includes a group of the formula:

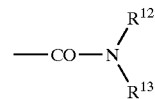

wherein $R^{12}$ and $R^{13}$ are the same or different and each is hydrogen, lower alkyl, phenyl which may have a suitable substituent selected from the group consisting of lower alkoxy and halogen, phenyl (lower) alkyl, pyridyl, pyridyl (lower)alkyl or 3,4-methylenedioxyphenyl;

aliphatic acyl such as lower alkanoyl which may be substituted by oneto three halogen atoms (e.g., formyl, acetyl, propanoyl, butanoyl, 2-methylpropanoyl, pentanoyl, 2,2-dimethylpropanoyl, hexanoyl, trichloroacetyl, trifluoroacetyl, etc.), lower alkoxycarbonyl (e.g., methoxycarbonyl, ethoxycarbonyl, tert-butoxycarbonyl, tert-pentyloxycarbonyl, etc.), lower alkylsulfonyl (e.g., methylsulfonyl, ethylsulfonyl, etc.), lower alkoxysulfonyl (e.g., methoxysulfonyl, ethoxysulfonyl, etc.), cyclo(lower)alkylcarbonyl (e.g., cyclopentylcarbonyl, cyclohexylcarbonyl, etc.), and the like;

aromatic acyl such as aroyl (e.g., benzoyl, toluoyl, naphthoyl, etc.), aryl(lower)alkanoyl [e.g., phenyl (lower)alkanoyl (e.g., phenylacetyl, phenylpropanoyl, phenylbutanoyl, etc.), naphthyl(lower)alkanoyl (e.g., naphthylacetyl, naphthylpropanoyl, naphthylbutanoyl, etc.), etc.], aryl(lower)alkoxycarbonyl [e.g., phenyl (lower)alkoxycarbonyl (e.g., benzyloxycarbonyl, etc.), etc.], aryloxycarbonyl (e.g., phenoxycarbonyl, naphthyloxycarbonyl, etc.), aryloxy(lower)alkanoyl (e.g., phenoxyacetyl, phenoxypropionyl, etc.), arylsulfonyl (e.g., phenylsulfonyl, p-tolylsufonyl, etc.), and the like;

heterocyclic acyl such as indolylcarbonyl (e.g., indolyl-2-yl-carbonyl, etc.), benzofuranylcarbonyl (e.g., benzofuran-2-yl-carbonyl), quinoxalinylcarbonyl, quinolylcarbonyl, pyrrolylcarbonyl, benzimidazolylcarbonyl, benzothienylcarbonyl, benzothiazolylcarbonyl, imidazolylcarbonyl, pyridylcarbonyl, morpholinylcarbonyl (e.g., morpholinocarbonyl) and the like. Optionally protected hydroxy" includes hydroxy and protected hydroxy. Suitable examples of "hydroxy protective group" in the term "protected hydroxy" include acyl (e.g., acetyl, trichloroacetyl, etc.), mono(or di or tri)phenyl(lower)alkyl which may have one or more suitable substituent(s) (e.g., benzyl, 4-methoxybenzyl, trityl, etc.), trisubstituted silyl [e.g., tri(lower)alkylsilyl (e.g., trimethylsilyl, tert-butyl-dimethylsilyl, etc.), etc.], tetrahydropyranyl and the like.

Suitable "protected carboxy" is carboxy group protected by conventional protective group such as lower alkoxycarbonyl [e.g., methoxycarbonyl, ethoxycarbonyl, propoxycarbonyl, isopropoxycarbonyl, butoxycarbonyl, sec-butoxycarbonyl, isobutoxycarbonyl, tert-butoxycarbonyl, pentyloxycarbonyl, neopentyloxycarbonyl, hexyloxycarbonyl, etc.], optionally substituted phenyl (lower)alkoxycarbonyl for exemple, mono- or di- or triphenyl(lower)alkoxycarbonyl which may be substituted by nitro [e.g., benzyloxycarbonyl, 4-nitrobenzyloxycarbonyl, benzhydryloxycarbonyl, trityloxycarbonyl, etc.] and the like.

Suitable "cyclo(lower)alkyl" includes cycloalkyl having 3 to 6 carbon atoms, such as cyclopropyl, cyclobutyl, cyclopentyl and cyclohexyl, in which more preferred ones are cyclopropyl and cyclobutyl.

The term "morpholinyl" includes 2-morpholinyl, 3-morpholinyl and 4-morpholinyl (i.e. morpholino).

The term piperidyl" includes 1-piperidyl (i.e. piperidino), 2-piperidyl, 3-piperidyl and 4-piperidyl.

And further, the compound having the following formula (II) is also exemplified as the preferable one of the "compound possessing an inhibitory activity on the production of nitric oxide".

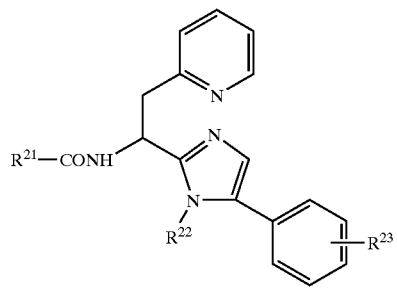

(II)

wherein, $R^{21}$ is benzofuranyl having halogen, $R^{22}$ is lower alkyl, and $R^{23}$ is morpholinyl.

The compound (I) and (II) usable in the present invention can be prepared in a similar manner to that of WO98/27108 (PCT/JP97/04243), the disclosure of which is incorporated herein by reference.

It is to be noted that the compound (I), (II) and other compounds may include one or more stereoisomer(s) such as optical isomer(s) and geometrical isomer(s) due to asymmetric carbon atom(s) and double bond(s), and all of such isomers and mixtures thereof are included within the scope of this invention.

The compound (I), (II) and pharmaceutically acceptable salts thereof can be in a form of solvates [e.g., hydrate, ethanolate, etc.], which are included within the scope of the present invention.

And further, the compound (I), (II) and pharmaceutically acceptable salts thereof can be in a form of pro-drugs, suitable derivatives, and so on.

The compound (I), (II) and pharmaceutically acceptable salts thereof possesses a strong inhibitory activity on the production of nitric oxide (NO). They are expected to possess a nitric oxide synthase (NOS)-inhibitory activity or a NOS-production inhibitory activity.

And further, the compounds shown in EP 0 394 989-A2, WO 96/16981, WO 97/45425, the Japanese Patent publication No. 10-45751, the Japanese patent application No. 9-160128, and so on, can also be used as "the compound possessing the inhibitory activity on the production of nitric oxide".

The "IL-2 inhibitor" used in the present invention should not be limited and be considered to mean any ones possessing IL-2 inhibitory activity. The particular example is the one possessing an inhibitory activity on the production of IL-2. And the other is the one that inhibits the transmission of IL-2 signal.

IL-2 is known to mediate immune system. Therefore, the preferable "effect caused by interleukin 2 inhibitor" is an immunosuppressive activity. Particularly, "the effect caused by interleukin 2 inhibitor" may be the treatment and prevention of rejection by transplantation, Graft-versus-Host diseases by medulla ossium transplantation, autoimmune diseases, and so on. And the present invention is useful to suppress immune reaction, to prolong the survival period of the graft, to reduce the administration amount of IL-2 inhibitor, and/or to reduce undesirable side effects caused by IL-2 inhibitor.

Preferable "IL-2 inhibitor" is, for example, the tricyclic macrolide shown in EP-0184162, WO89/05303, WO93/05058, WO96/31514, and so on, the disclosure of which is incorporated herein by reference. It is well known that those tricyclic macrolides have strong IL-2 inhibitory activity.

As a particular example of the tricyclic macrolides compounds, the tricyclic compound of the following formula (III) can be exemplified.

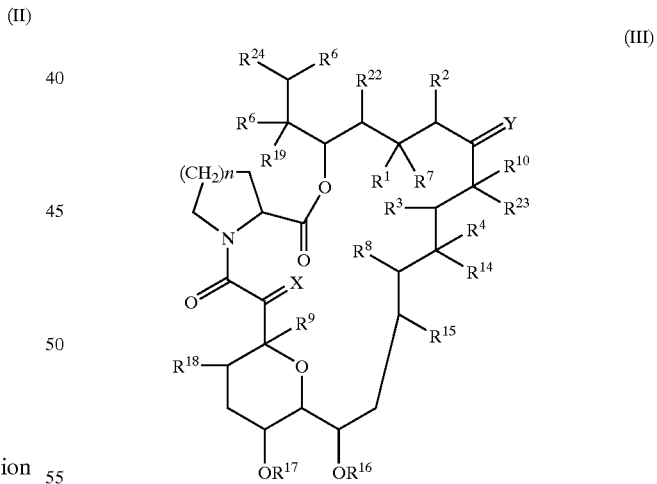

(III)

(wherein each of adjacent pairs of $R^1$ and $R^2$, $R^3$ and $R^4$, and $R^5$ and $R^6$ independently (a) is two adjacent hydrogen atoms, but $R^2$ may also be an alkyl group or (b) may form another bond formed between the carbon atoms to which they are attached;

$R^7$ is a hydrogen atom, a hydroxy group, a protected hydroxy group, or an alkoxy group, or an oxo group together with $R^1$;

$R^8$ and $R^9$ are independently a hydrogen atom or a hydroxy group;

$R^{10}$ is a hydrogen atom, an alkyl group, an alkyl group substituted by one or more hydroxy groups, an alkenyl group, an alkenyl group substituted by one or more hydroxy groups, or an alkyl group substituted by an oxo group;

X is an oxo group, (a hydrogen atom and a hydroxy group), (a hydrogen atom and a hydrogen atom), or a group represented by the formula —CH$_2$O—;

Y is an oxo group, (a hydrogen atom and a hydroxy group), (a hydrogen atom and a hydrogen atom), or a group represented by the formula N—NR$^{11}$R$^{12}$ or N—OR$^{13}$;

$R^{11}$ and $R^{12}$ are independently a hydrogen atom, an alkyl group, an aryl group or a tosyl group;

$R^{13}$, $R^{14}$, $R^{15}$, $R^{16}$, $R^{17}$, $R^{18}$, $R^{19}$, $R^{22}$ and $R^{23}$ are independently a hydrogen atom or an alkyl group;

$R^{24}$ is an optionally substituted ring system which may contain one or more heteroatoms;

n is an integer of 1 or 2; and in addition to the above definitions, Y, $R^{10}$ and $R^{23}$, together with the carbon atoms to which they are attached, may represent a saturated or unsaturated 5- or 6-membered nitrogen, sulfur and/or oxygen containing heterocyclic ring optionally substituted by one or more groups selected from the group consisting of an alkyl, a hydroxy, an alkoxy, a benzyl, a group of the formula —CH$_2$Se(C$_6$H$_5$), and an alkyl substituted by one or more hydroxy groups.

Preferable $R^{24}$ may be cyclo (C$_{5-7}$) alkyl group, and the following ones can be exemplified.

(a) a 3,4-di-oxo-cyclohexyl group;

(b) a 3-R$^{20}$-4-R$^{21}$-cyclohexyl group,
   in which $R^{20}$ is hydroxy, an alkoxy group, an oxo group, or a —OCH$_2$OCH$_2$CH$_2$OCH$_3$ group, and $R^{21}$ is hydroxy, —OCN, an alkoxy group, a heteroaryloxy which may be substituted by suitable substituents, a —OCH$_2$OCH$_2$CH$_2$OCH$_3$ group, a protected hydroxy group, chloro, bromo, iodo, aminooxalyloxy, an azido group, p-tolyloxythiocarbonyloxy, or R$^{25}$R$^{26}$CHCOO—,
   in which $R^{25}$ is optionally protected hydroxy or protected amino, and $R^{26}$ is hydrogen or methyl, or
   $R^{20}$ and $R^{21}$ together form an oxygen atom in an epoxide ring; or (c) cyclopentyl group substituted by methoxymethyl, optionally protected hydroxymethyl, acyloxymethyl (in which the acyl moiety optionally contains either a dimethylamino group which may be quaternized, or a carboxy group which may be esterified), one or more amino and/or hydroxy groups which may be protected, or aminooxalyloxymethyl. A preferred example is a 2-formyl-cyclopentyl group.

The definitions used in the above general formula (III) and the specific and preferred examples thereof are now explained and set forth in detail.

The term "lower" means, unless otherwise indicated, a group having 1 to 6 carbon atoms.

Preferable examples of the "alkyl groups" and an alkyl moiety of the "alkoxy group" include a straight or branched chain aliphatic hydrocarbon residue, for example, a lower alkyl group such asmethyl, ethyl, propyl, isopropyl, butyl, isobutyl, pentyl, neopentyl and hexyl.

Preferable examples of the "alkenyl groups" include a straight or branched chain aliphatic hydrocarbon residue having one double-bond, for example, a lower alkenyl group such as vinyl, propenyl (e.g., allyl group), butenyl, methylpropenyl, pentenyl and hexenyl.

Preferable examples of the "aryl groups" include phenyl, tolyl, xylyl, cumenyl, mesityl and naphthyl.

Preferable protective groups in the "protected hydroxy groups" and the "protected amino" are 1-(lower alkylthio) (lower)alkyl group such as a lower alkylthiomethyl group (e.g., methylthiomethyl, ethylthiomethyl, propylthiomethyl, isopropylthiomethyl, butylthiomethyl, isobutylthiomethyl, hexylthiomethyl, etc.), more preferably C$_1$–C$_4$ alkylthiomethyl group, most preferably methylthiomethyl group;

trisubstituted silyl group such as a tri(lower)alkylsilyl (e.g., trimethylsilyl, triethylsilyl, tributylsilyl, tert-butyldimethylsilyl, tri-tert-butylsilyl, etc.) or lower alkyl-diarylsilyl (e.g., methyldiphenylsilyl, ethyldiphenylsilyl, propyldiphenylsilyl, tert-butyldiphenylsilyl, etc.), more preferably tri(C$_1$–C$_4$) alkylsilyl group and C$_1$–C$_4$ alkyldiphenylsilyl group, most preferably tert-butyldimethylsilyl group and tert-butyldiphenylsilyl group; and an acyl group such as an aliphatic, aromatic acyl group or an aliphatic acyl group substituted by an aromatic group, which are derived from a carboxylic acid, sulfonic acid or carbamic acid.

Examples of the aliphatic acyl groups include a lower alkanoyl group optionally having one or more suitable substituents such as carboxy, e.g., formyl, acetyl, propionyl, butyryl, isobutyryl, valeryl, isovaleryl, pivaloyl, hexanoyl, carboxyacetyl, carboxypropionyl, carboxybutyryl, carboxyhexanoyl, etc.; a cyclo(lower)alkoxy(lower) alkanoyl group optionally having one or more suitable substituents such as lower alkyl, e.g., cyclopropyloxyacetyl, cyclobutyloxypropionyl, cycloheptyloxybutyryl, menthyloxyacetyl, menthyloxypropionyl, menthyloxybutyryl, menthyloxypentanoyl, menthyloxyhexanoyl, etc.; a camphorsulfonyl group; or a lower alkylcarbamoyl group having one or more suitable substituents such as carboxy or protected carboxy, for example, carboxy(lower)alkylcarbamoyl group (e.g., carboxymethylcarbamoyl, carboxyethylcarbamoyl, carboxypropylcarbamoyl, carboxybutylcarbamoyl, carboxypentylcarbamoyl, carboxyhexylcarbamoyl, etc.), tri(lower)alkylsilyl(lower)alkoxycarbonyl(lower) alkylcarbamoyl group (e.g., trimethylsilylmethoxycarbonylethylcarbamoyl, trimethylsilylethoxycarbonylpropylcarbamoyl, triethylsilylethoxycarbonylpropylcarbamoyl, tert-butyldimethylsilylethoxycarbonylpropylcarbamoyl, trimethylsilylpropoxycarbonylbutylcarbamoyl, etc.) and so on.

Examples of the aromatic acyl groups include an aroyl group optionally having one or more suitable substituents such as nitro, e.g., benzoyl, toluoyl, xyloyl, naphthoyl, nitrobenzoyl, dinitrobenzoyl, nitronaphthoyl, etc.; and an arenesulfonyl group optionally having one or more suitable substituents such as halogen, e.g., benzenesulfonyl, toluenesulfonyl, xylenesulfonyl, naphthalenesulfonyl, fluorobenzenesulfonyl, chlorobenzenesulfonyl, bromobenzenesulfonyl, iodobenzenesulfonyl, etc.

Examples of the aliphatic acyl groups substituted by an aromatic group include a (lower)alkanoyl group optionally having one or more suitable substituents such as lower alkoxy or trihalo(lower)alkyl, e.g., phenylacetyl, phenylpropionyl, phenylbutyryl, 2-trifluoromethyl-2-methoxy-2-phenylacetyl, 2-ethyl-2-trifluoromethyl-2-phenylacetyl, 2-trifluoromethyl-2-propoxy-2-phenylacetyl, etc.

More preferable acyl groups among the aforesaid acyl groups are C$_1$–C$_4$ alkanoyl group optionally having carboxy, cyclo(C$_5$–C$_6$)alkoxy(C$_1$–C$_4$)alkanoyl group having two (C$_1$–C$_4$) alkyls at the cycloalkyl moiety, camphorsulfonyl group, carboxy(C$_1$–C$_4$)alkylcarbamoyl group, tri(C$_1$–C$_4$) alkylsilyl(C$_1$–C$_4$)alkoxycarbonyl(C$_1$–C$_4$)alkylcarbamoyl group, benzoyl group optionally having one or two nitro groups, benzenesulfonyl group having halogen, or phenyl (C$_1$–C$_4$)alkanoyl group having C$_1$–C$_4$ alkoxy and trihalo ($C_1$–$C_4$)alkyl group. Among these, the most preferable ones are acetyl, carboxypropionyl, menthyloxyacetyl, camphorsulfonyl, benzoyl, nitrobenzoyl, dinitrobenzoyl, iodobenzenesulfonyl and 2-trifluoromethyl-2-methoxy-2-phenylacetyl.

Preferable examples of the "5- or 6-membered nitrogen, sulfur and/or oxygen containing heterocyclic ring" include a pyrrolyl group and a tetrahydrofuryl group.

The tricyclic compounds (III) and its pharmaceutically acceptable salt for use in accordance with this invention are well known to have excellent immunosuppressive activity, antimicrobial activity and other pharmacological activities and, as such, be of value for the treatment or prevention of rejection reactions by transplantation of organs or tissues, graft-vs-host diseases, autoimmune diseases, and infectious diseases [EP-A-0184162, EP-A-0323042, EP-A-423714, EP-A-427680, EP-A-465426, EP-A-480623, EP-A-532088, EP-A-532089, EP-A-569337, EP-A-626385, WO89/05303, WO93/05058, WO96/31514, WO91/13889, WO91/19495, WO93/5059, etc.].

Particularly, the compounds which are designated as FR900506 (=FK506), FR900520 (ascomycin), FR900523, and FR900525 are products produced by microorganisms of the genus Streptomyces, such as *Streptomyces tsukubaensis* No. 9993 [deposited with National Institute of Bioscience and Human Technology Agency of Industrial Science and Technology (formerly Fermentation Research Institute Agency of Industrial Science and Technology ), at 1-3, Higashi 1-chome, Tsukuba-shi, Ibaraki, Japan, date of deposit Oct. 5, 1984, accession number FERM BP-927] or *Streptomyces hygroscopicus* subsp. yakushimaensis No. 7238 [deposited with National Institute of Bioscience and Human Technology Agency of Industrial Science and Technology (formerly Fermentation Research Institute Agency of Industrial Science and Technology ), at 1-3, Higashi 1-chome, Tsukuba-shi, Ibaraki, Japan, date of deposit Jan. 12, 1985, accession number FERM BP-928] [EP-A-0184162]. The FK506 (general name: tacrolimus) of the following chemical formula, in particular, is a representative compound.

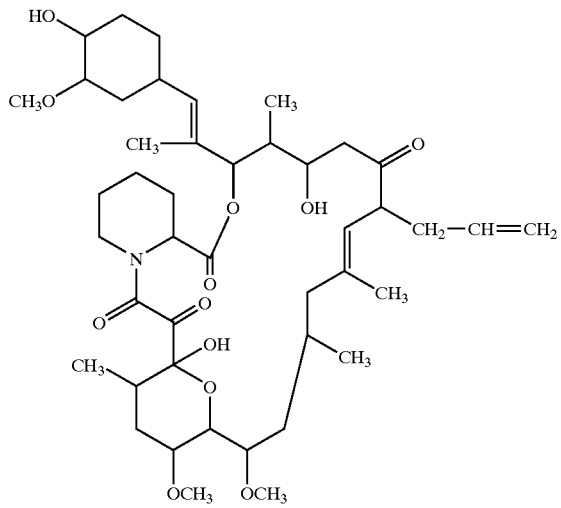

Chemical name: 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The preferred examples of the tricyclic compounds (III) are the ones, wherein each of adjacent pairs of $R^3$ and $R^4$ or $R^5$ and $R^6$ independently form another bond formed between the carbon atoms to which they are attached;

each of $R^8$ and $R^{23}$ is independently a hydrogen atom;

$R^9$ is a hydroxy group;

$R^{10}$ is a methyl group, an ethyl group, a propyl group or an allyl group;

X is (a hydrogen atom and a hydrogen atom) or an oxo group;

Y is an oxo group;

each of $R^{14}$, $R^{15}$, $R^{16}$, $R^{17}$, $R^{18}$, $R^{19}$, and $R^{22}$ is a methyl group;

$R^{24}$ is a 3-$R^{20}$-4-$R^{21}$-cyclohexyl group, in which $R^{20}$ is hydroxy, an alkoxy group, an oxo group, or a —$OCH_2OCH_2CH_2OCH_3$ group, and $R^{21}$ is hydroxy, —OCN, an alkoxy group, a heteroaryloxy which may be substituted by suitable substituents, a —$OCH_2OCH_2CH_2OCH_3$ group, a protected hydroxy group, chloro, bromo, iodo, aminooxalyloxy, an azido group, p-tolyloxythiocarbonyloxy, or $R^{25}R^{26}$CHCOO—, in which $R^{25}$ is optionally protected hydroxy or protected amino, and $R^{26}$ is hydrogen or methyl, or $R^{20}$ and $R^{21}$ together form an oxygen atom in an epoxide ring; and n is an integer of 1 or 2.

The most preferable tricyclic compounds (III) is, in addition to FK506, ascomycin derivatives such as halogenated-ascomycin (e.g., 33-epi-chloro-33-desoxyascomycin), which is disclosed in EP 427,680, example 66a.

As the other preferable example of the IL-2 inhibitor, rapamycin [THE MERCK INDEX (12th edition), No. 8288] and its derivatives can be exemplified. Preferred example of the derivatives is an O-substituted derivative in which the hydroxy in position 40 of formula A illustrated at page 1 of WO 95/16691, incorporated herein by reference, is replaced by —$OR_1$ in which $R_1$ is hydroxyalkyl, hydroalkoxyalkyl, acyiaminoalkyl and aminoalkyl; for example 40-O-(2-hydroxy)ethyl-rapamycin, 40-O-(3-hydroxy)propyl-rapamycin, 40-O-[2-(2-hydroxy)ethoxy]ethyl-rapamycin and 40-O-(2-acetaminoethyl)rapamycin. These O-substituted derivatives may be produced by reacting rapamycin (or dihydro or deoxo-rapamycin) with an organic radical attached to a leaving group (for example RX where R is the organic radical which is desired as the O-substituent, such as an alkyl, allyl, or benzyl moiety, and X is a leaving group such as $CCl_3C(NH)O$ or $CF_3SO_3$) under suitable reaction conditions. The conditions may be acidic or neutral conditions, for example in the presence of an acid like trifluoromethanesulfonic acid, camphorsulfonic acid, p-toluenesulfonic acid or their respective pyridinium or substituted pyridinium salts when X is $CCl_3C(NH)O$ or in the presence of a base like pyridine, a substituted pyridine, diisopropylethylamine or pentamethylpiperidine when X is $CF_3SO_3$. The most preferable one is 40-O-(2-hydroxy)ethyl rapamycin, which is disclosed in WO94/09010, the disclosure of which is incorporated herein by reference.

The tricyclic compounds (III), and rapamycin and its derivatives, may be in a form of its salt, which includes conventional non-toxic and pharmaceutically acceptable salt such as the salt with inorganic or organic bases, specifically, an alkali metal salt such as sodium salt and potassium salt, an alkali earth metal salt such as calcium salt and magnesium salt, an ammonium salt and an amine salt such as triethylamine salt and N-benzyl-N-methylamine salt.

With respect to the IL-2 inhibitor of the present invention, particularly the tricyclic macrolide compounds, it is to be understood that there may be conformers and one or more stereoisomers such as optical and geometrical isomers due to asymmetric carbon atom(s) or double bond(s), and such conformers and isomers are also included within the scope of the present invention. And further, the tricyclic macrolide compounds can be in the form of a solvate, which is included within the scope of the present invention. The solvate preferably include a hydrate and an ethanolate.

Further example of the IL-2 inhibitor is cyclosporin and its derivatives such as cyclosporin A, B, C, D, E, F, G, etc, which are shown in THE MERCK INDEX (12thedition), No. 2821, U.S. Pat. Nos. 4,117,118, 4,215,199, 4,288,431, 4,388,307, Helv. Chim. Acta. 60, 1568(1977) and 65, 1655 (1982), Transplant. Proc. 17, 1362(1985), and so on. Among which, the most preferable one is cyclosporin A. The disclosures of the above references are incorporated herein.

The tricyclic compounds (III) and its pharmaceutically acceptable salts, and cyclosporin or its derivatives may be classified as "IL-2 production inhibitor", which show immunosuppressive activity by inhibiting the production of IL-2. And rapamycin or its derivatives may be classified as "IL-2 signal transmission inhibitor", which show immunosuppressive activity by inhibiting the transmission of IL-2 signal.

For therapeutic administration, the compound possessing the inhibitory activity on the production of nitric oxide in the present invention is used in the form of a conventional pharmaceutical preparation in admixture with a conventional pharmaceutically acceptable carrier such as an organic or inorganic solid or liquid excipient which is suitable for oral, parenteral or external administration. The pharmaceutical preparation may be compounded in a solid form such as granule, capsule, tablet, dragee, suppository or ointment, or in a liquid form such as solution, suspension or emulsion for injection, intravenous drip, ingestion, eye drop, etc. If needed, there may be included in the above preparation auxiliary substance such as stabilizing agent, wetting or emulsifying agent, buffer or any other commonly used additives.

The "compound possessing the inhibitory activity on the production of nitric oxide" as the effective ingredient may usually be administered in a amount which can inhibit the production of nitric oxide. In particular, it may be a unit dose of 0.001 mg/kg to 500 mg/kg, preferably 0.01 mg/kg to 10 mg/kg, 1 to 4 times a day. However, the above dosage may be increased or decreased according to age, body weight and conditions of the patient or administering method.

If advisable, the compound possessing an inhibitory activity on the production of nitric oxide can be mixed with the IL-2 inhibitor prior to its use. So, the composition comprising the said compound possessing the inhibitory activity on the production of nitric oxide of the present invention may further comprise the IL-2 inhibitor. And optionally, it comprises further additional ingredients, such as, mycophenolatemofetil (CellCept), steroids, Azathiopurine, and so on.

The following Preparations and Examples are given for the purpose of illustrating the present invention in detail.

In the following Examples and Preparations, there are employed the other abbreviations in addition to the abbreviations adopted by the IUPAC-IUB (Commission on Biological Nomenclature).

The abbreviations used are as follows.

Boc: tert-butoxycarbonyl
Me: methyl
Et: ethyl
Pr: propyl
i-Pr: isopropyl
Bu: butyl
Ph: phenyl
Ts: p-toluenesulfonyl
Ac: acetyl
Bn: benzyl
Cbz: benzlyoxycarbonyl
Tf: trifluoromethanesulfonyl The starting compounds used and the compounds obtained in the following Preparations are given in the Tables as below, in which the formula of the starting compounds are in the left and the formula of the object compounds are in the right, respectively.

| Preparation No. | Formula |
|---|---|
| | starting compound — object compound |
| 1 | (structure) — (structure) |
| 2 | (structure) — (structure) |

-continued

| Preparation No. | Formula | |
|---|---|---|
| | starting compound | object compound |
| 3 | | |
| 4 | | |
| 5 | | |
| 6 | | |
| 7 | | |

-continued

| Preparation | Formula | |
|---|---|---|
| No. | starting compound | object compound |
| 8 | | |

PREPARATION 1

A solution of the starting compound (669 mg) and 40% methylamine(0.7 ml) in a mixture of acetic acid (0.7 ml) and xylene (7 ml) was refluxed for 4 hours ina flask equipped with a Dean-Stark trap. The mixture was concentrated, neutralized with 1N sodium hydroxide solution, and extracted three times with chloroform. The organic layer was washed with brine, dried over magnesium sulfate, filtered and concentrated. The residue was purified by column chromatography (silica gel, chloroform/methanol=50/1) to give the object compound as an oil (445 mg).

MASS (ESI) (m/z): 288 (M+H)$^+$; $^1$H-NMR (CDCl3, 300 MHz) δ: 1.46(9H, s), 3.60(3H, s), 4.48(2H, d, J=5 Hz), 5.33(1H, br s), 6.99(1H, s), 7.30–7.52(5H, m).

PREPARATION 2

To a solution of the starting compound (3.10 g) in methanol (15 ml) was added concentrated hydrochloric acid (3 ml), and the mixture was heated to 50° C. for 2 hours. The mixture was concentrated, made basic with a 1N sodium hydroxide solution, and extracted three times with chloroform. The organic layer was dried over magnesium sulfate, and filtered. Evaporation of the solvent gave the object compound(2.35 g).

MASS (ESI) (m/z): 308 (M+H)$^+$; $^1$H-NMR (CDCl3, 300 MHz) δ: 3.02–3.22(2H, m), 3.21(3H, s), 3.78(3H, s), 4.11 (1H, t, J=7 Hz), 6.81(2H, d, J=8 Hz), 6.99(2H, d, J=8 Hz), 7.04(1H, s), 7.21–7.48(5H, m).

PREPARATION 3

To an ice-cooled mixture of the starting compound (599 mg), 2-aminoacetophenone hydrochloride (362 mg) and 1-hydroxy-benzotriazole (270 mg) in dichloromethane (6 ml) was added 1-(3-dimethylamino-propyl)-3-ethylcarbodiimide (349 mg). The mixture was stirred at room temperature for 12 hours. A saturated aqueous sodium hydrogencarbonate solution was added to the mixture, and then the mixture was extracted three times with chloroform. The organic layer was washed with brine, dried over magnesium sulfate, filtered, and concentrated. The residue was purified by column chromatography (silica gel, chloroform/methanol=70/1) to give the object compound (823 mg).

MASS (ESI) (m/z): 417 (M+H)$^+$; $^1$H-NMR (CDCl3, 300 MHz) δ: 1.41(9H, s), 2.96–3.20(2H, m), 4.47(1H, m), 4.70 (2H, AB of ABX, JAB=15 Hz), 5.01(1H, br s), 6.92(1H, br s), 7.13(2H, d, J=8 Hz), 7.24(2H, d, J=8 Hz), 7.41–7.68(3H, m), 7.88–8.00(2H, m).

PREPARATION 4

The object compound was obtained according to a similar manner to that of Preparation 3.

oil; MASS: 450 (M+1); $^1$H-NMR (CDCl3) δ: 1.42(9H, s), 3.20–3.30(1H, m), 3.31–3.42 (1H, m), 4.62–4.73(1H, m), 4.70(2H, d, J=6 Hz), 6.42(1H, br s), 7.15(1H, t, J=6 Hz), 7.21(1H, d, J=6 Hz), 7.23(1H, s), 7.33(1H, s), 7.50(2H, d, J=8 Hz), 7.60(1H, t, J=8 Hz), 7.97(1H, s), 8.00(1H, br s), 8.08(2H, d, J=8 Hz), 8.57 (1H, d, J=8 Hz).

PREPARATION 5

The object compound was obtained according to a similar manner to that of Preparation 1.

MASS (ESI) (m/z): 473 (M+H)$^+$; $^1$H-NMR (CDCl3, 300 MHz) δ: 0.76(3H, t, J=7 Hz), 1.38(9H, s), 1.40–1.60(2H, m), 3.48–3.80(2H, m), 3.88–4.08(2H, m), 5.40–5.60(2H, m), 7.02–7.65(10H, m), 7.92(1H, s), 8.52 (1H, d, J=5 Hz).

PREPARATION 6

The object compound was obtained according to a similar manner to that of Preparation 2.

MASS (ESI) (m/z): 373 (M+H)$^+$; $^1$H-NMR (CDCl3, 300 MHz) δ: 0.78(3H, t, J=7 Hz), 1.36–1.72 (2H, m) 3.42–3.74 (2H, m), 3.85–4.24 (2H, m), 4.81–5.02 (1H, m), 7.08(1H, s), 7.15–7.72(9H, m), 7.93(1H, s), 8.55 (1H, d, J=5 Hz).

PREPARATION 7

To an ice-cooled solution of the starting compound (100 mg) indole-2-carboxylic acid (50 mg) and 1-hydroxybenzotriazole (41.9 mg) in dichloromethane (10 ml) was added 1-(3-dimethylaminopropyl)-3-ethylcarbodiimide hydrochloride (71.4 mg). The mixture was stirred at room temperature for 12 hours. A saturated aqueous sodium hydrogencarbonate solution was added to the mixture, and then the mixture was extracted three times with chloroform. The organic layer was washed with brine, dried over magnesium sulfate, filtered and concentrated. The residue was purified by column chromatography (silica gel, chloroform/methanol=70/1) to give the object compound as white powder (50 mg).

MASS (m/z): 466 (M+1); $^1$H-NMR (CDCl3) δ: 1.43(3H, t, J=7 Hz), 3.48(3H, s), 3.60(2H, m), 4.03(2H, q, J=7 Hz), 5.97(1H, m), 6.91(2H, d, J=8 Hz), 6.94(1H, s), 6.99(1H, s), 7.10–7.12(3H, m), 7.17(2H, d, J=8 Hz), 7.37(1H, d, J=8 Hz), 7.50(1H, t, J=8 Hz), 7.63(1H, d, J=8 Hz), 9.41(1H, s).

PREPARATION 8

The compound was obtained according to a similar manner to that of Preparation 7.

MASS (ESI) (m/z): 516 (M+H)$^+$; $^1$H-NMR (DMSO-d6, 300 MHz) δ: 0.64(3H, t, J=7 Hz), 1.31–1.55(2H, m), 3.41–3.67(2 H, m), 3.90–4.28(2H, m), 5.86–6.00(1H, m), 6.97–7.21(5H, m), 7.27(1H, s), 7.29–7.42(2H, m), 7.53(2H, d, J=8 Hz), 7.55–7.68(2H, m), 7.73(2H, d, J=8 Hz), 7.81(1H, s), 8.32(1H, s), 8.49(1H, d, J=5 Hz), 9.09(1H, br d, J=8 Hz), 10.50(1H, br s).

PREPARATION 9

To a solution of 2-amino-1-(4-morpholin-4-ylphenyl) ethan-1-one dihydrochloride (3.71 g), (2S)-(tert-butoxycarbonylamino)-3-(2-pyridyl)propanoic acid (5.73 g) and diphenylphosphoryl azide (3.48 g) in N,N-dimethylformamide (70 ml) was added dropwise N,N-diisopropylethylamine (4.41 ml) at 0° C. and the mixture was stirred for 20 minutes. The mixture was heated to ambient temperature and stirred for 8 hours. The resulting mixture was diluted with ethyl acetate (200 ml) and washed successively with water, a saturated aqueous sodium hydrogencarbonate solution and brine. The organic layer was dried over magnesium sulfate and concentrated in vacuo. The residual solid was triturated with ethyl acetate-diisopropyl ether (1: 2) to give (2S)-(tert-butoxycarbonylamino)-N-[2-(4-morpholin-4-ylphenyl)-2-oxoethyl]-3-(2-pyridyl)-propanamide (2.06 g) as off-white crystals.

ESI-NS; 469 (M+H); $^1$H-NMR (300 MHz, CDCl3) δ 1.46(9H, s), 3.20–3.38(6H, m), 3.82–3.88(4H, m), 4.60(2H, d, J=5 Hz), 4.64–4.74 (1H, br), 6.37–6.45(1H, br), 6.86(2H, d, J=9 Hz), 7.14(1H, dd, J=5,8 Hz), 7.21 (1H, d, J=8 Hz), 7.59(1H, t, J=8 Hz), 7.82–7.90(3H, m), 8.56 (1H, d, J=5 Hz).

PREPARATION 10

To a solution of (2S)-(tert-butoxycarbonylamino)-N-[2-(4-morpholin-4-ylphenyl)-2-oxoethyl]-3-(2-pyridyl)-propanamide (2.0 g) in acetic acid (4.0 ml) and xylene (60 ml) was added methylamine (40% in water, 4.0 ml) and the mixture was refluxed for 3 hours in a round-bottomed flask equipped with a Dean-Stark apparatus. The mixture was cooled to ambient temperature and a mixture of acetic acid (4.0 ml) and methylamine (40% in water, 4.0 ml) was added to the solution. The solution was refluxed for 2 hours and cooled to ambient temperature. The solution was extracted with 1N hydrochloric acid (100 ml) and the aqueous layer was washed with ethyl acetate (50 ml). The aqueous layer was made basic with a saturated aqueous sodium hydrogencarbonate solution and extracted with ethyl acetate (100 ml). The organic layer was washed successively with an aqueous sodium hydrogencarbonate solution and brine, dried over magnesium sulfate and concentrated in vacuo. The residue was purified by silica gel column chromatography (eluent; 2% methanol in chloroform) to give (1S)-(tert-butoxy)-N-[1-[1-methyl-5-(4-morpholin-4-ylphenyl)imidazol-2-yl]-2-(2-pyridyl)ethyl]formamide (1.45 g) as yellow crystals.

ESI-MS; 464 (M+H); $^1$H-NMR (300 MHz, CDCl3) δ 1.37(9H, s), 3.17–3.23(4H, m), 3.40(3H, s), 3.41–3.47(2H, m), 3.83–3.92(4H, m), 5.33–5.47(2H, m), 6.93(1H, s), 6.94 (2H, d, J=9 Hz), 7.08–7.16(2H, m), 7.21 (2H, d, J=9 Hz), 7.56(1H, t, J=8 Hz), 8.55(1H, d, J=5 Hz).

PREPARATION 11

To a solution of (1S)-(tert-butoxy)-N-[1-[1-methyl-5-(4-morpholin-4-ylphenyl)imidazol-2-yl]-2-(2-pyridyl)ethyl] formamide (1.43 g) in dichloromethane (25 ml) was added trifluoroacetic acid (5.0 ml) at 0° C. and the mixture was stirred at ambient temperature for 2.5 hours. The resulting mixture was concentrated in vacuo and the residue was dissolved in water (20 ml). The aqueous layer was made basic with a saturated aqueous sodium hydrogencarbonate solution and extracted with chloroform (80 ml). The organic layer was dried over magnesium sulfate and concentrated in vacuo. The residue was triturated with ethyl acetate-diisopropyl ether (1:2) to give (1S)-[1-methyl-5-(4-morpholin-4-ylphenyl)imidazol-2-yl]-2-(2-pyridyl)-ethylamine (1.02 g) as yellow crystals.

ESI-MS; 364 (M+H); $^1$H-NMR (300 MHz, CDCl3) δ 3.17–3.23(4H, m), 3.27–3.47(2H, m), 3.49(3H, s), 3.84–3.91 (4H, m), 4.58(1H, dd, J=5,8 Hz), 6.95(2H, d, J=9 Hz), 6.97(1H, s), 7.11–7.18(2H, m), 7.23(2H, d, J=9 Hz), 7.59(1H, t, J=8 Hz), 8.58(1H, d, J=5 Hz).

PREPARATION 12

To a solution of (1S)-[1-methyl-5-(4-morpholin-4-ylphenyl)imidazol-2-yl]-2-(2-pyridyl)ethylamine (120 mg), 5-chlorobenzo[d]furan-2-carboxylic acid (68.1 mg) and 1-hydroxybenzotriazole (49.1 mg) in N,N-dimethylformamide (2.0 ml) was added 1-(3-dimethylaminopropyl)-3-ethylcarbodiimide hydrochloride (69.6 mg). The mixture was stirred at ambient temperature for 2 hours and allowed to stand overnight. The resulting mixture was diluted with water (20 ml) and extracted with ethyl acetate (25 ml). The organic layer was extracted with 1N hydrochloric acid (15 ml) and the aqueous layer was made basic with a saturated aqueous sodium hydrogencarbonate solution, then extracted with ethyl acetate (20 ml). The organic layer was washed with brine, dried over magnesium sulfate and concentrated in vacuo. The residual solid was treated with hot acetonitrile (1.5 ml) and the mixture was cooled to ambient temperature. The solid was collected by filtration and washed with acetonitrile to give (1S)-(5-chlorobenzo[d]furan-2-yl)-N-[1-[1-methyl-5-(4-morpholin-4-ylphenyl)imidazol-2-yl]-2-(2-pyridyl)ethyl]formamide (89 mg) as off-white crystals.

mp 162–164° C.; ESI-MS; 542 (M+H); $^1$H-NMR (300 MHz, DMSO-d6) δ 3.11–3.17(4H, m), 3.42–3.60(2H, m), 3.53(3H, s), 3.70–3.77(4H, m), 5.83(1H, q, J=8 Hz), 6.88 (1H, s), 6.99(2H, d, J=9 Hz), 7.18(1H, dd, J=5,8 Hz), 7.26(2H, d, J=9 Hz), 7.30(1H, d, J=8 Hz), 7.47(1H, d, J=8 Hz), 7.59(1H, s), 7.63(1H, d, J=8 Hz), 7.68(1H, d, J=8 Hz), 7.87(1H, s), 8.48(1H, d, J=5 Hz), 9.32(1H, d, J=8 Hz); [α]D=171.90 (CHCl3, c=1.030%).

PREPARATION 13

In order to illustrate the activity of the compounds (I) and (II) the pharmacological test result of the representative compounds (a)–(g) of the compound (I) and (II), which were obtained in a similar manner to that of the above-mentioned Preparations and/or the above-identified WO 98/27108 (PCT/JP97/04243), are shown in the following.

Test Compounds:

(a)
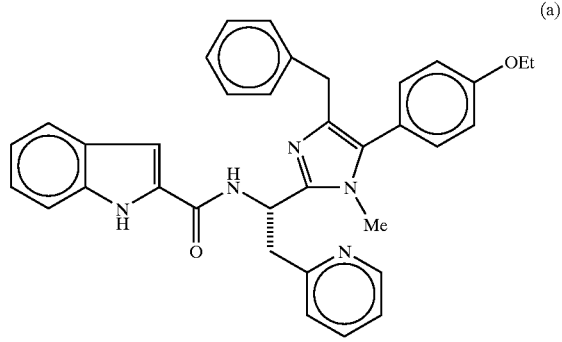

(b)
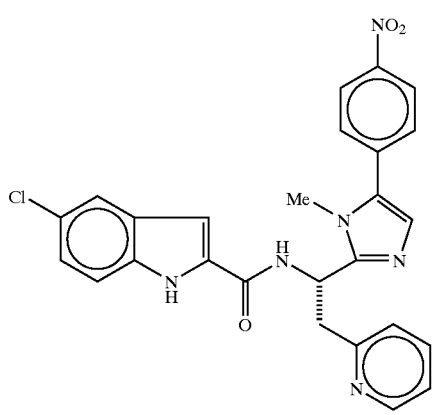

(c)
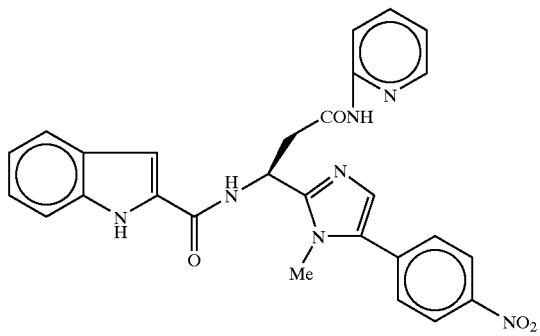

(d)
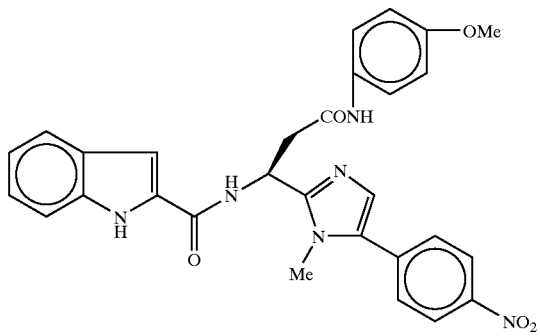

(e)
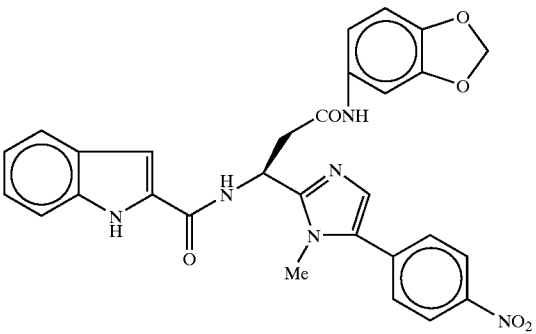

(f)
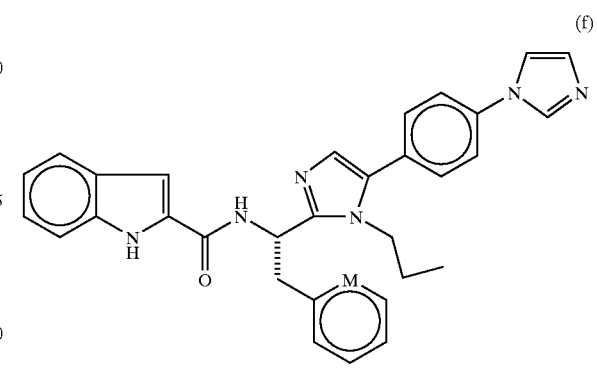

(g)
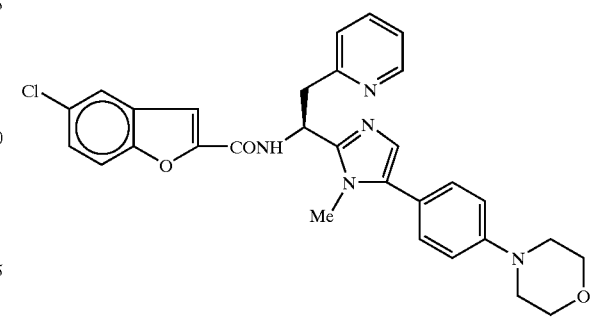

Test: Assay for Inhibitory Activity on the Production of Nitric Oxide

The murine macrophage cell line RAW264.7 (American Type Culture Collection, No. TIB71) was used in this study. RAW264.7 cells were grown on F75 plastic culture flasks at 37° C., 5% in Dulbecco's modified Eagle's medium (DMEM) supplemented with L-glutamine, penicillin, streptomycin and 10% heat-inactivated fetal bovine serum. They were removed from culture flasks by rubber cell scraper and were centrifuged and resuspended in DMEM without phenol red. They were plated in 96-well microtiter plates ($10^5$ cells per well) and allowed to adhere over 2 hours. The test samples were added and the cells were preincubated for 1 hour. Thereafter the cells were activated with both of lipopolysaccharide (LPS) (1 μg/ml) and interferon γ (INFγ) (3 u/ml) for 18–24 hours. An equal volume of Griess reagent (1% sulfanilamide/0.1% N-naphthylethylenediamine dihydrochloride/2.5% $H_3PO_4$) was added and the cells were incubated at room temperature for 10 minutes. The absorbance was read at 570 nm using microplate reader and $NO_2$ was measured using $NaNO_2$ as a standard.

Test result

| Test compound($10^{-5}$ M) | Inhibition (%) |
|---|---|
| (a) | 100 |
| (b) | 100 |
| (c) | 100 |
| (d) | 100 |
| (e) | 100 |
| (f) | 100 |
| (g) | 100 |

EXAMPLE 1

Protective effect of the compound (f) or (g) combined with FK506 on rat cardiac allograft:

(Method)

Experiments were performed on male Lewis and ACI rats weighing 175–200 g. Rats were anesthetized with sodium pentobarbital (50 mg/kg, i.p), and performed allogeneic (Lewis donor to ACI recipient) heterotopic intra-abdominal cardiac transplantation. Experimental groups were divided into single-drug group and combined-drug groups. Single-drug dose of FK506 was 0.32 mg/kg. Combined-dose groups were FK506(0.32 mg/kg)+the compound (f) (3.2 mg/kg), FK506(0.32 mg/kg)+the compound (f) (10 mg/kg), and FK506(0.32 mg/kg)+the compound (g) (10 mg/kg). The grafted hearts were monitored by daily palpation and complete rejection was defined as the cessation of palpable contractile activity. Drugs were suspended in a solution of 0.5% methylcellulose, and administered by daily gastric intubation in a volume of 5 ml/kg of body weight for 14 days. The blood samples were collected on 5 days after transplantation for analysis of nitrite/nitrate (NOx). The concentration of NOx in rat plasma was measured by using a spectrophotometric assay based upon the Griess reaction.

(Result)

The compounds (f) or (g), which was used in the preparation 13, was examined in combination with a potent immunosuppressive agent (FK506) to determine whether they could improve rat cardiac allograft survival.

Graft survival and the concentration of NOx are shown in the following tables 1 and 2.

TABLE 1

Protective effect of the compound (f) combined with FK506 on rat cardiac allograft.

| Test compound(s) | n | MST (day) | NOx ($\mu$M) |
|---|---|---|---|
| FK506 (0.32 mg/kg) | 12 | 8.5 | >40 |
| Compound (f) (3.2 mg/kg) + FK506 (0.32 mg/kg) | 11 | 12 | <30 |
| Compound (f) (10 mg/kg) + FK506 (0.32 mg/kg) | 12 | >40### | <30 |

Significant vs. FK506 (0.32 mg/kg) at ###: $p < 0.001$ by Mann-Whitney test.
Significant vs. FK506 (0.32 mg/kg) at *: $p < 0.05$, **: $p < 0.01$ by Mann-Whitney test.
MST: Median Survival Time

TABLE 2

Protective effect of the compound (g) combined with FK506 on rat cardiac allograft.

| Test compound | n | MST (day) |
|---|---|---|
| FK506 (0.32 mg/kg) | 6 | 10 |
| Compound (g) (10 mg/kg) + FK506 (0.32 mg/kg) | 9 | >30 |

The elevated NOx production during cardiac allograft rejection was inhibited by the compound (f) or (g) in a dose-dependent manner. The combination of the compound (f) or (g) and FK506 dramatically prolonged the graft survival. These results indicate that NOx plays a pivotal role in the regulation of graft survival and the compound (f) or (g) is good candidates for combination with FK506 on allograft model.

The major immune mechanisms of cellular allograft rejection are T lymphocyte-mediated cytotoxicity and delayed-type hypersensitivity. The effector cells of delayed-type hypersensitivity are macrophages and nitric oxide generated by iNOS in macrophages has been demonstrated to have cytotoxicity to allograft.

It is known that FK506 and cyclosporine A inhibit immune reaction mediated by lymphocytes at a low dose, but they do not strongly inhibit nitric oxide production by iNOS in macrophages.

According to the present invention, allograft rejection could remarkably and/or synergistically be reduced by suppression of nitric oxide production by macrophages and further by suppression of cytotoxic T cell.

Particularly, the present invention is quite useful for treating and/or preventing acute rejection after transplantation.

While the effective dosage of the IL-2 inhibitor depends on the type of the said IL-2 inhibitor, the patient's age, type of disease, severity of illness, and other factors, a daily dose thereof is about 0.01~1000 mg, preferably 0.05~500 mg, and more preferably, 0.1~100 mg for therapeutic purposes. The average unit dose may be generally about 0.1 mg, 0.5 mg, 1 mg, 5 mg, 10 mg, 50 mg, 100 mg, 250 mg, or 500 mg.

When the above-mentioned tricyclic macrolides is used as the IL-2 inhibitor in the present invention, the pharmaceutical composition of the present invention is useful for increasing the effect of the treatment and/or prevention of the following diseases and conditions because of the pharmacologic activities possessed by the said tricyclic macrolides.

Rejection reactions by transplantation of organs or tissues such as the heart, kidney, liver, bone marrow, skin, cornea, lung, pancreas, small intestine, limb, muscle, nerve, intervertebral disc, trachea, myoblast, cartilage etc.;

graft-versus-host reactions following bone marrow transplantation;

autoimmune diseases such as rheumatoid arthritis, systemic lupus erythematosus, Hashimoto's thyroiditis, multiple sclerosis, myasthenia gravis, type I diabetes, etc.;

and infections caused by pathogenic microorganisms (e.g. *Aspergillus fumigatus, Fusarium oxysporum, Trichophyton asteroides*, etc.);

Inflammatory or hyperproliferative skin diseases or cutaneous manifestations of immunologically-mediated diseases (e.g. psoriasis, atopic dermatitis, contact dermatitis, eczematoid dermatitis, seborrheic dermatitis, lichen planus, pemphigus, bullous pemphigoid, epidermolysis bullosa, urticaria, angioedema, vasculitides, erythema, dermal eosinophilia, lupus erythematosus, acne, and alopecia areata);

autoimmune diseases of the eye (e.g. keratoconjunctivitis, vernal conjunctivitis, uveitis associated with Behcet's disease, keratitis, herpetic keratitis, conical keratitis, corneal epithelial dystrophy, keratoleukoma, ocular premphigus, Mooren's ulcer, scleritis, Graves' ophthalmopathy, Vogt-Koyanagi-Harada syndrome, keratoconjunctivitis sicca(dry eye), phlyctenule, iridocyclitis, sarcoidosis, endocrine ophthalmopathy, etc.);

reversible obstructive airways diseases [asthma (e.g. bronchial asthma, allergic asthma, intrinsic asthma, extrinsic asthma, and dust asthma), particularly chronic or inveterate asthma (e.g. late asthma and airway hyper-responsiveness) bronchitis, etc.];

mucosal or vascular inflammations (e.g. gastric ulcer, ischemic or thrombotic vascular injury, ischemic bowel diseases, enteritis, necrotizing enterocolitis, intestinal damages associated with thermal burns, leukotriene B4-mediated diseases);

intestinal inflammations/allergies (e.g. coeliac diseases, proctitis, eosinophilic gastroenteritis, mastocytosis, Crohn's disease and ulcerative colitis);

food-related allergic diseases with symptomatic manifestation remote from the gastrointestinal tract (e.g. migrain, rhinitis and eczema);

renal diseases (e.g. intestitial nephritis, Goodpasture's syndrome, hemolytic uremic syndrome, and diabetic nephropathy); nervous diseases (e.g. multiple myositis, Guillain-Barre syndrome, Meniere's disease, multiple neuritis, solitary neuritis, cerebral infarction, Alzheimer's disease, Parkinson's disease, amyotrophic lateral sclerosis(ALS) and radiculopathy);

cerebral ischemic disease(e.g., head injury, hemorrhage in brain (e.g., subarachnoid hemorrhage, intracerebral hemorrhage), cerebral thrombosis, cerebral embolism, cardiac arrest, stroke, transient ischemic attack (TIA), hypertensive encephalopathy, cerebral infarction);

endocrine diseases (e.g. hyperthyroidism, and Basedow's disease); hematic diseases (e.g. pure red cell aplasia, aplastic anemia, hypoplastic anemia, idiopathic thrombocytopenic purpura, autoimmune hemolytic anemia, agranulocytosis, pernicious anemia, megaloblastic anemia, and anerythroplasia);

bone diseases (e.g. osteoporosis);

respiratory diseases (e.g. sarcoidosis, pulmonary fibrosis, and idiopathic interstitial pneumonia);

skin diseases (e.g. dermatomyositis, leukoderma vulgaris, ichthyosis vulgaris, photosensitivity, and cutaneous T-cell lymphoma);

circulatory diseases (e.g. arteriosclerosis, atherosclerosis, aortitis syndrome, polyarteritis nodosa, and myocardosis);

collagen diseases (e.g. scleroderma, Wegener's granuloma, and Sjogren's syndrome);

adiposis;

eosinophilic fasciitis;

periodontal diseases (e.g. damage to gingiva, periodontium, alveolar bone or substantia ossea dentis);

nephrotic syndrome (e.g. glomerulonephritis);

male pattern alopecia, alopecia senile;

muscular dystrophy;

pyoderma and Sezary syndrome;

chromosome abnormality-associated diseases (e.g. Down's syndrome);

Addison's disease;

active oxygen-mediated diseases [e.g. organ injury (e.g. ischemic circulation disorders of organs (e.g. heart, liver, kidney, digestive tract, etc.) associated with preservation, transplantation, or ischemic diseases (e.g. thrombosis, cardial infarction, etc.)):

intestinal diseases (e.g. endotoxin shock, pseudomembranous colitis, and drug- or radiation-induced colitis):

renal diseases (e.g. ischemic acute renal insufficiency, chronic renal failure):

pulmonary diseases (e.g. toxicosis caused by pulmonary oxygen or drugs (e.g. paracort, bleomycin, etc.), lung cancer, and pulmonary emphysema):

ocular diseases (e.g. cataracta, iron-storage disease (siderosis bulbi), retinitis, pigmentosa, senileplaques, vitreousscarring, corneal alkali burn):

dermatitis (e.g. erythema multiforme, linear immunoglobulin A bullous dermatitis, cement dermatitis):

and other diseases (e.g. gingivitis, periodontitis, sepsis, pancreatitis, and diseases caused by environmental pollution (e.g. air pollution), aging, carcinogen, metastasis of carcinoma, and hypobaropathy)];

diseases caused by histamine release or leukotriene C4 release; restenosis of coronary artery following angioplasty and prevention of postsurgical adhesions;

autoimmune diseases and inflammatory conditions (e.g., primary mucosal edema, autoimmune atrophic gastritis, premature menopause, male sterility, juvenile diabetes mellitus, pemphigus vulgaris, pemphigoid, sympathetic ophthalmitis, lens-induced uveitis, idiopathic leukopenia, active chronic hepatitis, idiopathic cirrhosis, discoid lupus erythematosus, autoimmune orchitis, arthritis (e.g. arthritis deformans), or polychondritis);

Human Immunodeficiency Virus (HIV) infection AIDS;

allergic conjunctivitis;

hypertrophic cicatrix and keloid due to trauma, burn, or surgery.

In addition, the said tricyclic macrolides have liver regenerating activity and/or activities of stimulating hypertrophy and hyperplasia of hepatocytes. Therefore, the pharmaceutical composition of the present invention is useful for increasing the effect of the therapy and/or prophylaxis of liver diseases [e.g. immunogenic diseases (e.g. chronic autoimmune liver diseases such as autoimmune hepatic diseases, primary biliary cirrhosis or sclerosing cholangitis), partial liver resection, acute liver necrosis (e.g. necrosis caused by toxins, viral hepatitis, shock, or anoxia), hepatitis B, non-A non-B hepatitis, hepatocirrhosis, and hepatic failure (e.g. fulminant hepatitis, late-onset hepatitis and "acute-on-chronic" liver failure (acute liver failure on chronic liver diseases))].

And further, the present composition is also useful for increasing the effect of the prevention and/or treatment of various diseases because of the useful pharmacological activity of the said tricyclic macrolides, such as augmenting activity of chemotherapeutic effect, activity of cytomegalovirus infection, anti-inflammatory activity, inhibiting activity against peptidyl-prolyl isomerase or rotamase, antimalarial activity, antitumor activity, and so on.

The patents, patent applications and publications cited herein are incorporated by reference.

What is claimed is:

1. A method for increasing graft survival time in a transplantation subject having a graft comprising:

administering to said subject:

a compound (a) that is a compound possessing an inhibitory activity on the production of nitric oxide and compound (b) that is a tricyclic macrolide or a salt, solvate or hydrate thereof, in an amount and for a time and under conditions effective to increase graft survival time, wherein said tricyclic macrolide has the following structure:

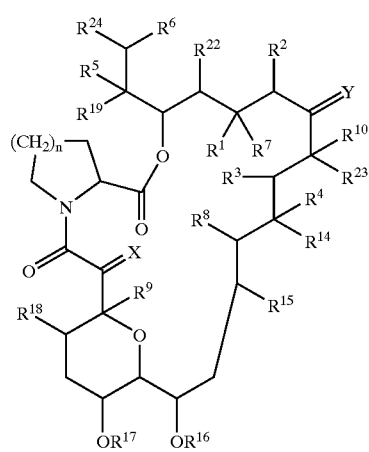

(III)

wherein each of the adjacent pairs $R^1$ and $R^2$, $R^3$ and $R^4$, and $R^5$ and $R^6$ are independently (a) two adjacent hydrogen atoms, but $R^2$ may also be an alkyl group, (b) or may form a bond between the carbon atoms to which they are attached, $R^7$ is a hydrogen atom, a hydroxy group, a protected hydroxy group or an alkoxy group or together with $R^1$ is an oxo group;

$R^8$ and $R^9$ are independently a hydrogen atom or hydroxy group;

$R^{10}$ is a hydrogen atom, an alkyl group, an alkyl group substituted by one or more hydroxy groups, an alkenyl group, an alkenyl group substituted by one or more hydroxy groups, or an alkyl group substituted by an oxo group;

X is an oxo group; a hydrogen atom and a hydroxy group; two hydrogen atoms; or a group represented by the formula —CH$_2$O—;

Y is an oxo group; a hydrogen atom and a hydroxyl group; two hydrogen atoms; or a group represented by the formula N—NR$^{11}$R$^{12}$ or N—OR$^{13}$;

$R^{11}$ and $R^{12}$ are independently a hydrogen atom, an alkyl group, an aryl group or a tosyl group;

$R^{13}$, $R^{14}$, $R^{15}$, $R^{16}$, $R^{17}$, $R^{18}$, $R^{19}$, $R^{22}$ and $R^{23}$ are independently a hydrogen atom or an alkyl group;

$R^{24}$ is a ring system that may contain one or more heteroatoms and may be substituted;

n is an integer of 1 or 2;

wherein in addition to the above definitions,

Y, $R^{10}$ and $R^{23}$ together with the carbon atoms to which they are attached, may represent a saturated or unsaturated 5- or 6-membered nitrogen, sulfur and/or oxygen containing heterocyclic ring optionally substituted by one or more groups selected from the group consisting of an alkyl, a hydroxy, an alkoxy, a benzyl, a group of the formula —CH$_2$Se(C$_6$H$_5$), and an alkyl substituted by one or more hydroxy groups, wherein compound (a) is not compound (b).

2. A method for increasing graft survival time in a transplantation subject having a graft comprising:

administering to said subject:

a compound (a) that is a compound possessing an inhibitory activity on the production of nitric oxide and a compound (b) that is a tricyclic macrolide that is tacrolimus or a salt, solvate or hydrate thereof, in an amount and for a time and under conditions effective to increase graft survival time, wherein compound (a) is not compound (b) and wherein tacrolimus has the following structure:

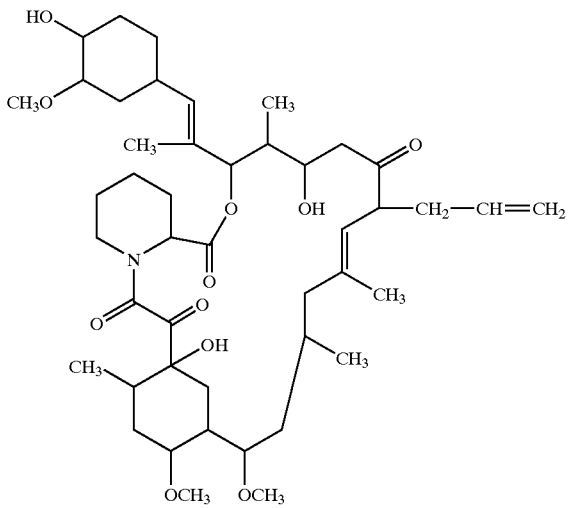

3. The method of claim 1, wherein compound (a) inhibits the production of inducible nitric oxide synthase.

4. The method of claim 1, wherein compound (a) inhibits inducible nitric oxide synthase.

5. The method of claim 1, wherein compound (a) has chemical formula (I):

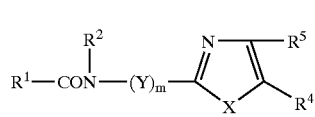

(I)

wherein $R^1$ is:

indolyl which may have a substituent selected from the group consisting of: lower alkyl, phenyl, halogen, lower alkoxy, and nitro, benzofuranyl, phenyl which may have one or two substituent(s) selected from the group consisting of amino, acylamino, lower alkylamino, halogen, lower alkoxy and nitro, lower alkyl,
quinoxalinyl,
quinolyl,
pyrrolyl,
pyrimidinyl having benzofuranyl,
benzimidazolyl,
benzothienyl,
benzothiazolyl,
benzoxazolyl,
indolinyl,
anilino,
phenylcarbamoyl or
imidazolyl which may have one or two substituent(s) selected from the group consisting of phenyl, lower alkyl and indolyl;

$R^2$ is hydrogen or phenyl(lower)alkyl;

$R^4$ is:
hydrogen, phenyl or pyridyl, each of which may have a substituent(s) selected from the group consisting of lower alkyl, lower alkoxy, lower alkylthio, halogen, trihalomethyl, nitro, cyano, imidazolyl, optionally protected hydroxy, acyl, amino, acylamino, diacylamino, di(lower)alkylamino, amino(lower)alkyl, acylamino(lower)alkyl, pyrazolyl, morpholinyl, piperidyl, triazolyl, lower alkoxy(lower)alkoxy, hydroxy(lower)alkyl, lower alkylpiperazinyl, phenyl and carboxy, quinolyl or 3,4-methylenedioxyphenyl;

$R^5$ is hydrogen, imidazolyl, phenyl, nitrophenyl, phenyl(lower)alkyl, optionally esterified carboxy or a group of the formula:

$$-CO-N\begin{matrix}R^7\\R^8\end{matrix}$$

in which
$R^7$ and $R^8$ are the same or different and each is hydrogen, phenyl, phenyl(lower)alkyl, lower alkyl or lower alkoxy; or $R^4$ and $R^5$ in combination form a group of the formula:

—CH=CH—CH=CH—

Y is a group of the formula:

$$-\overset{R^3}{\underset{|}{CH}}-$$

in which
$R^3$ is hydrogen or a group of the formula:

—(CH$_2$)$_n$—R$^6$ in which
$R^6$ is
optionally protected hydroxy,
acyl,
carboxy,
acylamino,
lower alkoxy,
phenyl(lower)alkoxy,
lower alkylthio,
phenyl which may have a substituent selected from the group consisting of lower alkoxy, halogen, amino, acylamino, diacylamino, and nitro,
pyridyl which may have a substituent selected from the group consisting of lower alkoxy and halogen,
pyrazinyl,
pyrimidinyl,
furyl,
imidazolyl,
naphthyl,
N-(lower)alkylindolyl or
3,4-methylenedioxyphenyl, and
n is an integer of 0 to 3, or a group of the formula:

in which
$R^{11}$ is phenyl, phenoxy or phenyl(lower)alkoxy; or $R^2$ and $R^3$ in combination form a group of the formula:

m is 0 or 1; and
X is S or NR$^9$
in which
$R^9$ is hydrogen, lower alkyl, cyclo(lower)alkyl or a group of the formula:

$$-CH_2-\phantom{X}-R^{10}$$

in which
$R^{10}$ is hydrogen, lower alkyl or lower alkoxy; or
a pharmaceutically acceptable salt thereof.

6. The method of claim 1, wherein compound (a) has chemical formula (II):

(II)

wherein
$R^{21}$ is benzofuranyl having halogen,
$R^{22}$ is lower alkyl, and
$R^{23}$ is morpholinyl.

7. The method of claim 1, wherein said graft is an allograft.

8. The method of claim 1, wherein said graft is a cardiac graft.

9. The method of claim 1, wherein said subject is suffering from acute rejection.

10. The method of claim 1, wherein compound (a) and compound (b) are simultaneously, separately or sequentially administered.

11. The method of claim 1, wherein compound (a) and compound (b) are separately administered.

12. The method of claim 1, wherein compound (a) and compound (b) are simultaneously administered.

* * * * *